(12) United States Patent
Park et al.

(10) Patent No.: US 11,810,312 B2
(45) Date of Patent: Nov. 7, 2023

(54) MULTIPLE INSTANCE LEARNING METHOD

(71) Applicant: DAEGU GYEONGBUK INSTITUTE OF SCIENCE AND TECHNOLOGY, Daegu (KR)

(72) Inventors: Sang Hyun Park, Daegu (KR); Philip Chikontwe, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 444 days.

(21) Appl. No.: 17/236,191

(22) Filed: Apr. 21, 2021

(65) Prior Publication Data
US 2021/0334994 A1 Oct. 28, 2021

(30) Foreign Application Priority Data

Apr. 21, 2020 (KR) .......................... 10-2020-0047888
Apr. 20, 2021 (KR) .......................... 10-2021-0051331

(51) Int. Cl.
*G06T 7/593* (2017.01)
*G06N 20/00* (2019.01)
(Continued)

(52) U.S. Cl.
CPC ............. *G06T 7/593* (2017.01); *G06N 20/00* (2019.01); *G06T 2207/10081* (2013.01);
(Continued)

(58) Field of Classification Search
CPC ......... G06T 2207/20081; G06T 7/0012; G06T 2207/20084; G06T 2207/30096;
(Continued)

(56) References Cited

U.S. PATENT DOCUMENTS 8,588,519 B2 * 11/2013 Liu ..................... G06F 18/2148
382/159
9,317,781 B2 * 4/2016 Tu ...................... G06V 10/7753
(Continued)

FOREIGN PATENT DOCUMENTS

KR 10-1925603 2/2019
KR 10-2020-0021082 2/2020
(Continued)

OTHER PUBLICATIONS

Wang et al., "Attention-based Multi-instance Neural Network for Medical Diagnosis from Incomplete and Low Quality Data", Jul. 2019 (Year: 2019).*
(Continued)

*Primary Examiner* — Dung Hong
(74) *Attorney, Agent, or Firm* — LEX IP MEISTER, PLLC

(57) ABSTRACT

A multiple instance learning device for analyzing 3D images, comprises a memory in which a multiple instance learning model is stored and at least one processor electrically connected to the memory, wherein the multiple instance learning model comprises a convolution block configured to derive a feature map for each of 2D instances of a 3D image inputted to the multiple instance learning model, a spatial attention block configured to derive spatial attention maps of the instances from the feature maps derived from the convolution block, an instance attention block configured to receive a result of combining the feature maps and the spatial attention maps and derive an attention score for each instance, and derive an aggregated embedding for the 3D image by aggregating embeddings of the instances according to the attention scores.

17 Claims, 10 Drawing Sheets

(51) Int. Cl.
*G16H 30/40* (2018.01)
*G16H 50/20* (2018.01)

(52) U.S. Cl.
CPC .............. *G06T 2207/20081* (2013.01); *G06T 2207/30061* (2013.01); *G16H 30/40* (2018.01); *G16H 50/20* (2018.01)

(58) Field of Classification Search
CPC . G06T 2207/30024; G06T 2207/10056; G06T 2207/10081; G06T 2207/20021; G06T 2200/04; G06T 2207/10072; G06N 20/00; G06N 3/08; G06N 3/045
See application file for complete search history.

(56) References Cited

U.S. PATENT DOCUMENTS

2009/0290802 A1* 11/2009 Hua .................. G06V 10/26
382/225
2022/0309653 A1* 9/2022 Hassanpour ........... G06V 10/82

FOREIGN PATENT DOCUMENTS

| KR | 10-2020-0035129 | 4/2020 |
| KR | 10-2020-0132665 | 11/2020 |
| KR | 10-2217159 | 2/2021 |
| KR | 10-2021-0030730 | 3/2021 |

OTHER PUBLICATIONS

Li et al., "Multi-Instance Multi-Scale CNN for Medical Image Classification", First Online: Oct. 10, 2019 (Year: 2019).*
Maximilian Ilse et al., "Attention-based Deep Multiple Instance Learning", arXiv, 1802.04712v4., International conference on machine learning. PMLR 80, 2018. (Jun. 28, 2018).
Kamyar Nazeri et al., "Two-stage convolutional neural network for breast cancer histology image classification." arXiv, 1803.04054v2. (Apr. 1, 2018).
KIPO, Notice of Allowance of Application No. 10-2020-0047888, dated Dec. 23, 2022.
Philip Chikontwe et al., "Multiple Instance Learning with Center Embeddings for Histopathology Classification", MICCAI 2020: Medical Image Computing and Computer Assisted Intervention—MICCAI 2020 pp. 519-528. https://doi.org/10.1007/978-3-030-59722-1_50.
Noriaki Hashimoto et al., "Multi-scale Domain-adversarial Multiple-instance CNN for Cancer Subtype Classification with Unannotated Histopathological Images", arXiv:2001.01599v2 [cs.CV] Apr. 2, 2020.
Gabriele Campanella et al., "Clinical-grade computational pathology using weakly supervised deep learning on whole slide images", Nat Med. Aug. 2019 ; 25(8): 1301-1309. doi:10.1038/s41591-019-0508-1.
Philip Chikontwe et al., "Dual Attention Multiple Instance Learning with Unsupervised Complementary Loss for COVID-19 Screening", Cold Spring Harbor Laboratory Press, 2020. https://doi.org/10.1101/2020.09.14.20194654.

* cited by examiner

FIG. 5

|       | DA-CMIL |     |
|-------|---------|-----|
|       | CP      | NCP |
| CP    | 40      | 0   |
| NCP   | 1       | 30  |

|       | DA-CMIL |     |
|-------|---------|-----|
|       | CP      | NCP |
| CP    | 35      | 5   |
| NCP   | 7       | 24  |

|       | DeepAttentionMIL |     |
|-------|------------------|-----|
|       | CP               | NCP |
| CP    | 30               | 10  |
| NCP   | 0                | 31  |

|       | JointMIL |     |
|-------|----------|-----|
|       | CP       | NCP |
| CP    | 34       | 6   |
| NCP   | 1        | 30  |

|       | Zhnag3DCNN |     |
|-------|------------|-----|
|       | CP         | NCP |
| CP    | 35         | 5   |
| NCP   | 0          | 31  |

DA-CMIL

| | CP | NCP |
|---|---|---|
| CP | 39 | 1 |
| NCP | 2 | 29 |

MIL

| | CP | NCP |
|---|---|---|
| CP | 32 | 8 |
| NCP | 3 | 28 |

DeepAttentionMIL

| | CP | NCP |
|---|---|---|
| CP | 30 | 10 |
| NCP | 1 | 30 |

JointMIL

| | CP | NCP |
|---|---|---|
| CP | 36 | 4 |
| NCP | 7 | 24 |

FIG. 11 (a)
FIG. 11 (b)
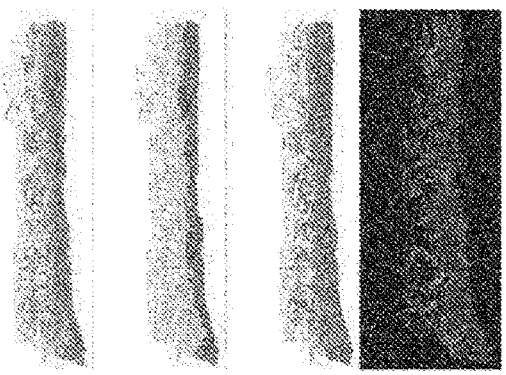
FIG. 11 (c)

MULTIPLE INSTANCE LEARNING METHOD

CROSS-REFERENCE TO RELATED APPLICATION

The present application claims the benefit of priority to Korean Patent Application No. 10-2020-0047888, entitled "MULTIPLE INSTANCE LEARNING FOR HISTOPATHOLOGY CLASSIFICATION," filed on Apr. 21, 2020, in the Korean Intellectual Property Office and Korean Patent Application No. 10-2021-0051331, entitled "DUAL ATTENTION MULTIPLE INSTANCE LEARNING METHOD," filed on Apr. 20, 2021, in the Korean Intellectual Property Office, the entire disclosure of which are incorporated herein by reference.

FIELD

The present disclosure relates to a dual attention multiple instance learning method, and more particularly, to a multiple instance learning method using unsupervised contrastive loss. Also, the present disclosure relates to a method for multiple instance learning for histopathology classification, and more particularly, to a method for multiple instance learning for histopathology classification capable of accurately predicting instance labels

BACKGROUND

Chest computed tomography (CT) based analysis and diagnosis of the Coronavirus Disease 2019 (COVID-19) plays a key role in combating the outbreak of the pandemic that has rapidly spread worldwide.

However, accurate screening is challenging due to the difficulty in annotation of infected areas, curation of large datasets, and the slight discrepancies between COVID-19 and other viral pneumonia.

Also, automated screening sensitivity is limited and not on par with radiologist level performance.

Therefore, there is an urgent need to improve and/or develop robust screening methods based on chest CT.

On the other hand, deep learning based solutions have shown success in medical image analysis due to the ability to extract rich features from clinical datasets, and include a wide range of application areas such as organ segmentation and disease diagnosis, etc.

Despite showing promising performance, most deep learning based methods are supervised and require considerable labeling efforts.

Therefore, unsupervised or weakly supervised learning methods that do not heavily rely on extensive data preprocessing and/or strong prior knowledge are a preferred option for accurate diagnosis Also, in recent times, digitizing glass slides into histopathological images using a whole-slide image (WSI) scanner is fulfilling an important role as a standard for cancer diagnosis in clinical settings.

A single WSI has a very large volume (i.e. 100 k pixels), and selective analysis thereof thus requires consideration of both the difficulty and the time consuming nature of analysis.

In particular, due to the high computational cost and the bias of subjective judgment of observers, automated and accurate analysis of WSIs is suitable for providing improved diagnostics and better treatment strategies.

Deep learning has become a widely-used solution, and can yield improved results when sufficient training data is provided.

However, there are limitations in that pixel level annotations are difficult and involve high costs.

In order to address such limitations, multiple instance learning (MIL)-based training of neural networks presents a solution that can alleviate the challenges relating to final WSI diagnosis without precise annotations.

Methods of performing histopathology classification using MIL-based training of neural networks have been proposed in, for example, Campanella, G., Hanna, M G, Geneslaw, L., Miraor, A., Silva, V W K, Busam, K J, Brogi, E., Reuter, V E, Klimstra, D S, and Fuchs, T J: Clinical-grade computational pathology using weakly supervised deep learning on whole slide images. Nature medicine 25(8), 1301-1309 (2019).

However, due to the ambiguity of instance labels in MIL, learning robust instance embeddings is very difficult.

To address this issue, Hashimoto, N., Fukushima, D., Koga, R., Takagi, Y., Ko, K., Kohno, K., Nakaguro, M., Nakamura, S., Hontani, H., and Takeuchi, I.: Multi-scale domain-adversarial multiple-instance cnn for cancer subtype classification with non-annotated histopathological images. arXiv preprint arXiv:2001.01599 (2020), for example, adopts a two-step approach that includes (1) learning an instance encoder based on sampled regions from the WSI, and (2) learning an aggregation model that uses the learned instance encoder to integrate instance level information for slide-level prediction.

However, even when the above two-stage approach is used, there are limitations in that, although this approach is successful in some problem settings, it often fails when learning is performed using a number of instances with ambiguous distinctions, and is worsened in the second stage of learning the aggregation model since features are not representative of the true labels.

Accordingly, accurate classification is difficult, and reliability of classification may be reduced.

SUMMARY

The present disclosure provides an attention-based end-to-end weakly supervised framework for the rapid diagnosis based on multiple instance learning (MIL).

Further, the present disclosure incorporates unsupervised contrastive learning for improved accuracy with attention applied both in spatial and latent contexts, and herein we propose Dual Attention Contrastive based MIL (DA-CMIL).

Also, the present disclosure provides approaches that use (a) patch-based (b) slice-based, and (c) 3D CT-based methods for diagnostic decisions.

In addition, the present disclosure provides a novel end-to-end attention-based weakly supervised framework using multiple instance learning (MIL) and self-supervised contrastive learning of features towards accurate diagnosis of COVID-19 from bacterial pneumonia.

Also, in order to address the limitations described above, the present disclosure is directed to providing a method for multiple instance learning for histopathology classification that enables more accurate classification by changing the aggregation model.

In addition, the present disclosure is directed to providing a method for multiple instance learning for histopathology classification that follows standard histopathology processes.

More specifically, the present disclosure is directed to providing an end-to-end model for histopathology classification that is capable of assigning correct instance and bag labels.

A multiple instance learning device for analyzing 3D images according to the present disclosure may comprise a memory in which a multiple instance learning model is stored and at least one processor electrically connected to the memory, wherein the multiple instance learning model comprises: a convolution block configured to derive a feature map for each of 2D instances of a 3D image inputted to the multiple instance learning model; a spatial attention block configured to derive spatial attention maps of the instances from the feature maps derived from the convolution block; an instance attention block configured to receive a result of convolving the feature maps and the spatial attention maps and derive an attention score for each instance, and derive an aggregated embedding for the 3D image by aggregating embeddings of the instances according to the attention scores; and an output block configured to output an analysis result for the 3D image based on the aggregated embedding.

Also, the at least one processor is configured to perform an operation of, in a training phase of the multiple instance learning model, training the multiple instance learning model such that a total loss function (L) of the multiple instance learning model has a minimum value, using training data including 3D images labeled as ground-truths for the analysis result.

Here, the total loss function is a combination of a bag-level loss function (LB) for a result of the output block and a contrastive loss function (LF) between the instance embeddings and the aggregated embedding.

A method for multiple instance learning for histopathology classification according to the present disclosure may be performed by at least one processor in a computing device or computing network, and may include: an instance selection step of implementing a feature extraction model $F_\theta(\cdot)$ to transform an instance $p_{ij}$ from an i-th slide into a low dimensional embedding $g_{ij}$, and after checking a positiveness of the instance $p_{ij}$ using a binary classifier, sorting the instance level probabilities of all bags and sampling topmost instances per slide for training; a learning step of learning using the instances obtained in the instance selection step, wherein instance-level learning and bag-level learning are performed sequentially to obtain a final loss; and a soft-assignment-based inference step of assigning a bag-level embedding $z_i$ to a learned centroid using a kernel that detects a similarity between two points.

The present disclosure enables more accurate analysis for 3D image while providing unsupervised or weakly supervised learning methods that do not heavily rely on extensive data pre-processing and/or strong prior knowledge.

Moreover, by jointly using a supervised and contrastive loss, our model can avoid overfitting when trained on smaller datasets and improve feature robustness at the instance level without sacrificing accuracy.

Also, multiple instance learning method according to the present disclosure can be robust to different CT sizes when instance (i.e. slice/patch) count varies.

The present disclosure has the effect of allowing more accurate classification, by improving bag feature learning via a center loss and also reducing uncertainty in instance labels.

In addition, by considering both instance-based MIL and embedding-based MIL, the present disclosure has the effect of improving classification performance and reducing false positives.

BRIEF DESCRIPTION OF THE DRAWINGS

The above and other aspects, features, and advantages of the present disclosure will become apparent from the detailed description of the following aspects in conjunction with the accompanying drawings, in which:

FIG. 5 illustrates graphs comparing prediction performances of the multiple instance learning model according to an embodiment of the present disclosure and other learning models on a CT slice dataset.

FIGS. 11(a), 11(b) and 11(c) show qualitative results of the method of another embodiment of the present disclosure in terms of two aspects: k patches, which are model samples per slide-class, and effectiveness of a learned model in interpretability via segmentation.

DETAILED DESCRIPTION

Figure 1:
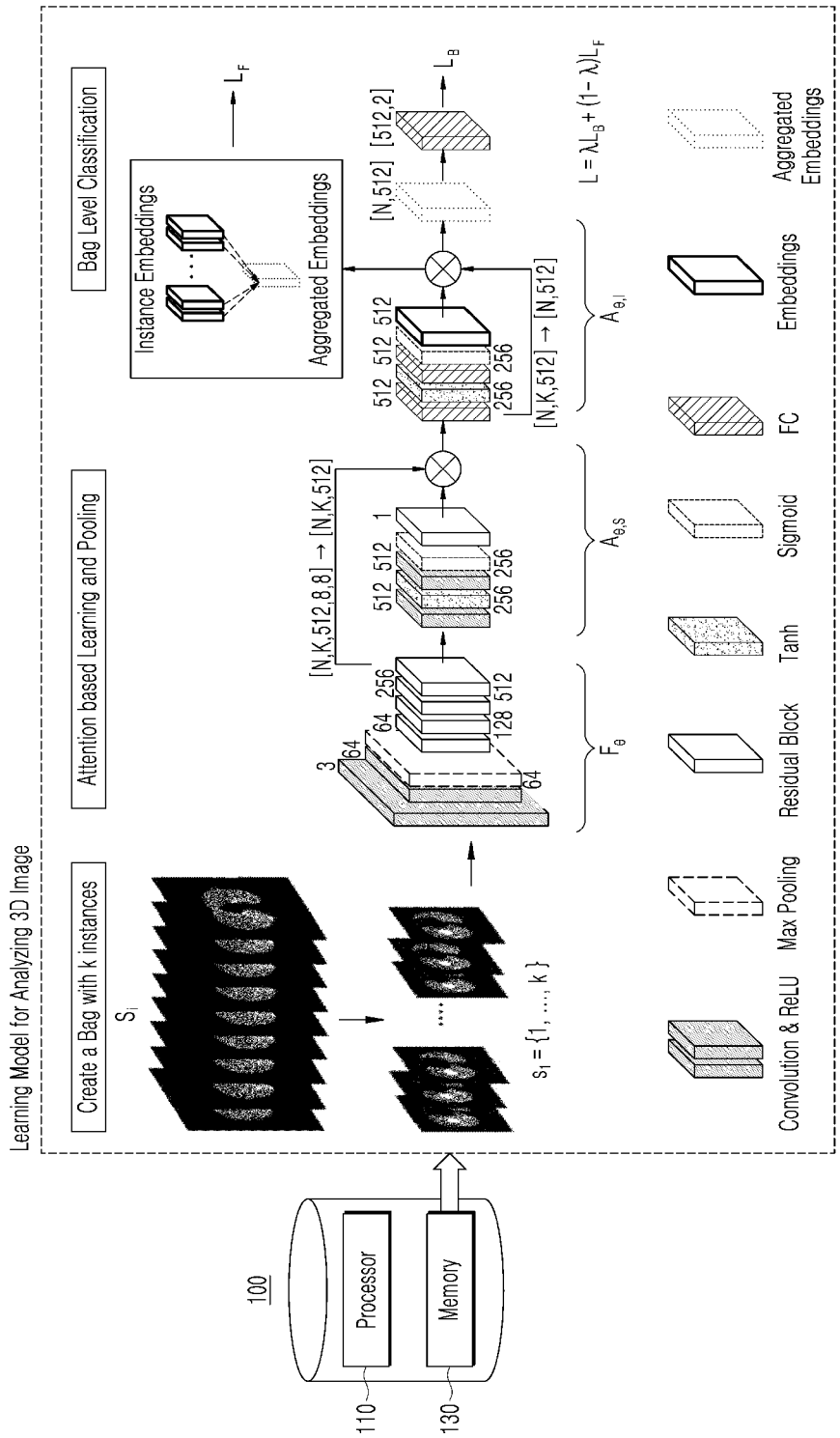
FIG. 1 illustrates a multiple instance learning device and a framework of a multiple instance learning model according to an embodiment of the present disclosure.

Hereinafter, preferred embodiments disclosed herein will be described in detail with reference to the accompanying drawings, in order to facilitate easy understanding of the configuration and effects of the present disclosure. However, the present disclosure is not limited to the embodiments disclosed herein, as the present disclosure may be implemented in various forms and various modifications may be made. The descriptions of the embodiments disclosed herein are provided so that this disclosure will be thorough and complete and will fully convey the scope of the present disclosure to those skilled in the art. For convenience of description, the sizes of the elements in the accompanying drawings are enlarged compared to their real forms, and the ratios of each element may be exaggerated or reduced.

'Furthermore, terms such as "first," "second," and other numerical terms, are used only to distinguish one element from another element. These terms may only be used to distinguish one element from another number. For example, without departing from the scope of the present disclosure, a "first element" may be referred to as a "second element", and similarly, a "second element" may also be referred to as a "first element". As used herein, the articles "a", "an", and "the" include plural referents unless the context clearly dictates otherwise. Unless otherwise defined, the terms used in the embodiments of the present disclosure may be interpreted in terms of the meanings thereof that are commonly known to those skilled in the art.

Multiple instance learning method and apparatus according to the present disclosure enables more accurate image analysis using dual attention blocks and contrastive loss function in addition to bag level loss function.

Even though multiple instance learning method and apparatus according to the present disclosure can be applied to various 3D image analysis, the concept of the present invention may be explained with illustrative cases for distinguishing between bacterial pneumonia and COVID-19 pneumonia using 3D CT image analysis.

Multiple instance learning according to the present disclosure can be referred to as Dual Attention Contrastive based MIL (DA-CMIL). DA-CMIL takes as input several patient CT slices (considered as bag of instances) from a 3D CT image and outputs a single label.

Attention based pooling is applied to implicitly select key slices in the latent space, whereas spatial attention learns slice spatial context for interpretable diagnosis. A contrastive loss is applied at the instance level to encode similarity of features from the same patient against representative pooled patient features.

The goal of DA-CMIL is to assign patients a single category label i.e. (COVID-19 or bacterial pneumonia) given as input a CT volume of multiple 2D slices.

In general, each patient CT scan is considered as a bag of instances that may be positive or negative. Moreover, it would be beneficial to identify which slices/instances contribute to the final patient diagnosis with the potential to localize infected regions.

The present disclosure proposes an attention based permutation-invariant MIL method for the pooling of slices to obtain a single representative feature of patients.

In addition, spatial attention is jointly applied to learn spatial features key for infection area discovery. The present disclosure incorporates contrastive learning at the instance level to encourage instance features from the same patient to be semantically similar to the patient level aggregated feature in an unsupervised manner.

To achieve this, an unsupervised contrastive loss is employed alongside patient category labels for the supervised loss during training.

Existing works using MIL applied in different domains often decouple instance and bag level learning into a two-step procedure i.e. first learn instance level encoders, then learn aggregation models for inference using the trained encoders with MIL pooling. However, due to the ambiguity of the instance labels and noise, learning a robust encoder can be challenging.

Thus, the framework according to the present disclosure aims to address the aforementioned challenges via end-to-end learning; instance selection is implicitly achieved via attention based pooling of CT slices with model optimization focused only on accurate patient labels.

The present disclosure provides a novel end-to-end model for weakly supervised classification of COVID-19 from bacterial pneumonia, and show that joint contrastive learning of instance features and patient level features in the MIL setting is viable.

FIG. 1 illustrates a multiple instance learning device and a framework of a multiple instance learning model according to an embodiment of the present disclosure.

An embodiment of the present disclosure considers a chest CT dataset $D=\{S_1, \ldots, S_n\}$ where the model receives a set of m labeled example scans $\{(S_i, y_i)\}_{i=1}^{m}$ drawn from the joint distribution defined by $S \times Y$. $S_i$ is a patient CT scan with instances (i.e. 2D CT slices or patches) and Y is the label set of patient-level labels, wherein Y is $\{0, 1\}$ for binary classification of COVID-19 and other.

Also, $S_i$ is considered as a bag of instances with $S_i=\{s_1, s_2, \ldots, s_N\}$ where N denotes the total number of instances in the bag.

It can be assumed that each instance $s_n$ has a label $y_n \in \{0, 1\}$, however not all instances may be negative or positive.

Moreover, not all slices in a scan may show infection regions vital for diagnosis, as others may be noisy artifacts not useful for learning.

Accordingly, MIL must satisfy the following constraints: if a bag $S_i$ is negative, then it can be assumed that all corresponding instances should be negative. In the case of positive bags, at least one instance is assumed to be positive. Formally, it follows that $$y = \begin{cases} 0, & \text{iff } \sum_n y_n = 0, \\ 1, & \text{otherwise} \end{cases} \quad \text{Equation 1}$$

In the present disclosure, this assumption may not hold given that both sets of bags (COVID-19 and other pneumonia) considered contain both negative and positive instances (lesions). Thus, the embodiment considers a relaxed version of this constraint wherein an attention mechanism is applied to implicitly weight instances and learn their labels.

The inventors of the present disclosure developed a CNN model for patient CT scan level diagnosis between COVID-19 and other pneumonia in a single end-to-end framework. Herein, a dual-attention multi-instance learning deep model with unsupervised contrastive learning (DA-CMIL) is proposed.

As presented in FIG. 1, the method according to the present disclosure takes a CT scan with unlabeled instances as input and learns key semantic representations. It further uses an attention-based pooling method to transform patient instances into a single bag representation for final prediction. Unsupervised contrastive learning is employed to encourage instances in a bag to be semantically similar to the bag representation during training.

In the proposed framework, a backbone CNN model $\mathcal{F}_\theta$ is implemented as a feature extractor to transform the j-th instance from a CT bag into a low dimension embedding $g_{ij} = \mathcal{F}_\theta(s_{ij})$ with spatial dimensions of shape $C \times H \times W$, where C, H and W are the channel size, height and width, respectively.

Following, $g_{ij}$ is feed to a spatial attention module $A_{\theta,S}$ in order to learn spatial representative features and output spatial attention maps of size $1 \times H^* \times W^*$ per instance with C=1.

The obtained maps highlight key regions and are further used to weight all the initial instances features to obtain a single spatial pooled feature $\phi_{ij} = \mathcal{A}_{\theta,S}(g_{ij})$, with $\phi \in \mathbb{R}^D$, where D is the feature dimension size (see Section 3.3). To aggregate the instance features $\phi_n$ for each CT scan, the embodiment of the present disclosure implements a second module $\mathcal{A}_{\theta,I}$ that performs attention-based permutation invariant pooling to obtain a single bag representation $z_{ij} = \mathcal{A}_{\theta,I}(\phi_{ij})$ with $z \in \mathbb{R}^D$ having the same dimension for consistency. Following, $z_n$ is passed to the patient level classifier $\mathcal{H}_B$ to obtain predictions for the entire bag $\hat{y} = \mathcal{H}_B(z_i)$, where $\hat{y}$ is the probability of a CT scan being labeled as COVID-19 or other pneumonia. Formally, the embodiment of the present disclosure employs the bag loss $\mathcal{L}_B(\hat{y}, y_i)$ using cross-entropy. It follows that $$\mathcal{L}_B = -\Sigma y_i \log \hat{y}. \quad \text{Equation 2}$$

Dual Attention based Learning

Attention has shown to be vital for learning robust features, especially under the MIL setting. In particular, attention-based pooling is preferred over existing pooling methods such as max or mean, since they are not differentiable/applicable for end-to-end model updates. The present disclosure implemented both spatial ($A_{\theta,S}$) and latent embedding ($A_{\theta,I}$) based attention pooling via the respective modules. In the spatial module, given the input $g_{ij} \in \mathbb{R}^{C \times H \times W}$ the present disclosure employs two convolutional layers each followed by hyperbolic tangent (tan h) and sigmoid (sigm) non-linearities, respectively.

Feature maps $g_{ij}$ are passed to each module successively, then to the final convolutional layer having a single channel output representing the presence of infection.

In particular, element-wise multiplication between the output of each branch of the convolutional layers is performed before passing it to the final layer to obtain spatial scores $\phi_{ij} \in \mathbb{R}^{1 \times H \times W}$. Following, the spatial scores are normalized by a softmax operation, with the final spatially pooled features obtained by a summed matrix multiplication across both height and weight dimensions i.e. $\phi'_{ij} = \phi_{ij} \times g_{ij}$, where $\phi'_{ij} \in \mathbb{R}^D$, though for consistency $\phi'_{ij}$ can be referred to as $\phi$. It is worth noting that the embodiment of the present disclosure simply implemented gated spatial attention instead of the commonly applied global average pooling (GAP) on the initial backbone features $g_n$. Moreover, the initial normalized spatial maps can be used to visually show the regions the model focuses on to make decisions.

In order to aggregate the features $\phi_n$, the embodiment of the present disclosure may employ attention based pooling proposed by Ilse et al. (2018) in the instance attention module $A_{\theta,I}$. Formally, the same architectural design previously applied for gated spatial attention on the initial backbone features may be considered, except all convolutional layers are replaced with fully connected layers since attention is applied to instance embeddings.

The present disclosure denotes $H = \{\phi_1, \phi_2, \phi_3, \ldots, \phi_N\}$, with $h_i \in H^N$ as a bag with N instance features. Then, attention based pooling MIL with gating mechanism is defined as $$z = \sum_{n}^{N} a_n h_n \quad \text{Equation 3}$$

with, $$a_n = \frac{\exp\{w^T(\tanh(Vh_n^T) \odot sigm(Uh_n^T))\}}{\sum_{j=1}^{N} \exp\{w^T(\tanh(Vh_j^T) \odot sigm(Uh_j^T))\}}, \quad \text{Equation 4}$$

where $w \in \mathbb{R}^{N \times 1}$, $V \in \mathbb{R}^{N \times D}$, and $U \in \mathbb{R}^{N \times D}$ are trainable parameters. $\tan h(\bullet)$ and $\text{sigm}(\bullet)$ are element wise non-linearities, with $\odot$ representing element-wise multiplication. In addition, $a_n$ is considered as the attention score per instance indicating the relevance of a given instance to the overall bag prediction.

From a technical standpoint, attention based pooling allows different weights to be assigned to instances alleviating the need for explicit instance selection. Moreover, the final bag representation will be more informative. The synergistic combination of spatial and attention based pooling allows for improved training towards learning robust and interpretable features.

Contrastive MIL

Figure 2:
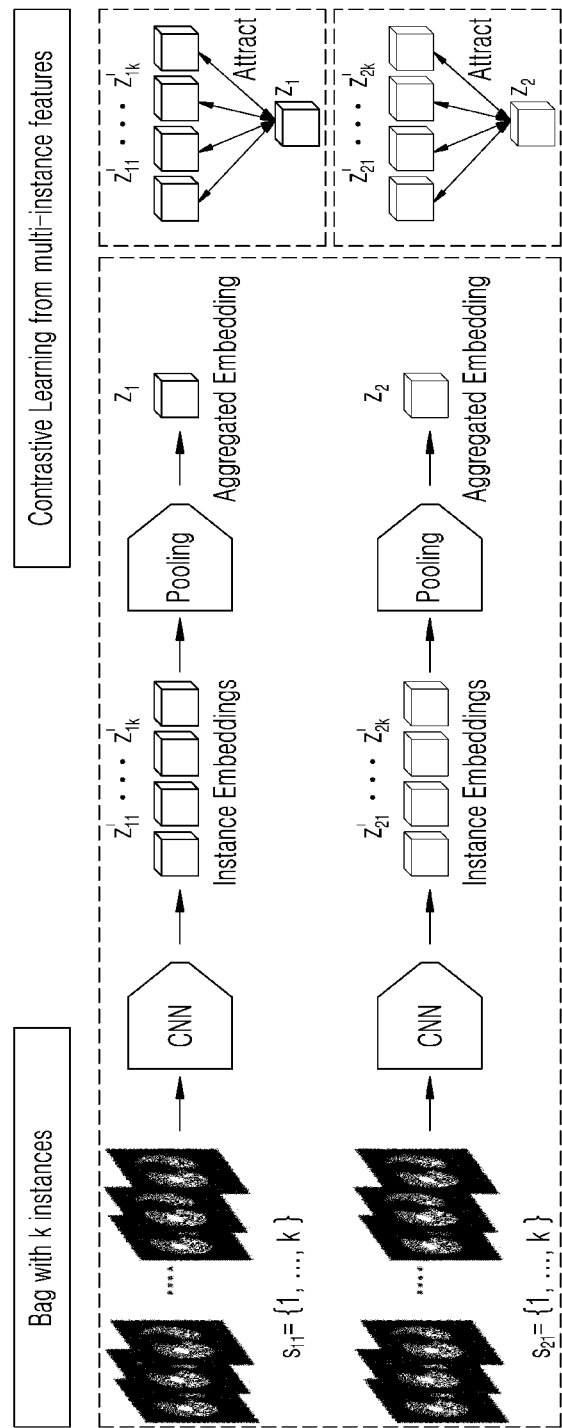
FIG. 2 is a diagram illustrating contrastive learning applied to a multiple instance learning setting according to an embodiment of the present disclosure.

FIG. 2 is a diagram illustrating contrastive learning applied to a multiple instance learning setting according to an embodiment of the present disclosure.

In an embodiment of the present disclosure, an unsupervised con-trastive loss is integrated with the proposed MIL method for improved learning of instance level features. Formally, the model according to the present disclosure learns representations that maximize the agreement between instance features and an aggregated bag feature of the same patient via a contrastive loss in the latent space. FIG. 2 shows the overall concept of the applied technique.

According to the previously proposed self-supervised framework that uses contrastive loss, stochastic data augmentation is applied on 2D data samples to create two correlated views of the same example. Augmentations include random cropping, color distortions and random Gaussian blurring. Moreover, the contrastive loss is proposed to define contrastive predictive tasks on unlabeled samples, wherein positive and negative pairs are identified for given samples. To incorporate this idea, stochastic data augmentation is omitted here since contrastive loss is applied in the latent space.

In addition, for any given patient CT scan; it is inferred that each slice can be considered as a pseudo augmentation of the overall patient characteristics. Thus, the present disclosure considers that stochastic augmentation is implicitly applied (i.e. different views of the same patient).

Let z' be the latent instance level feature of patient, and z the patient bag-level feature obtained via the proposed modules. Then, following $l_2$ normalization of z' and z features, a contrastive loss can be defined as $$\mathcal{L}_F(z', z, \tau) = -\log \sum_{i,j=1}^{N} \frac{\exp(sim(z'_i, z_j)/\tau)}{\sum_{k=1}^{2N} \mathbb{Q}_{[k \neq i]} \exp(sim(z'_i, z_k)/\tau)} \quad \text{Equation 5}$$

where $\mathbb{Q}_{[k \neq i]} \in \{0, 1\}$ is an indicator function that evaluates to 1(iff k≠i) and $\mathbb{Q}$ denotes a temperature parameter. Temperature parameter is a parameter to adjust the degree that the difference in similarity is reflected to loss, and temperature parameter can be empirically decided by using random numbers as an optimal variable. Sim($\bullet$, $\bullet$) is a similarity function i.e. cosine similarity. Here, $z_i$ and $z_j$ can mean feature of i-th patch(slice) and feature of j-th patch(slice). Also, N is the batch size defined in training phase, and the batch size becomes 2N when two data are compared like in FIG. 2, making the top number of sigma 2N. To obtain $\mathcal{L}_F$, feature map of each instance(i=1, . . . , the total number of instances) and the bag-level feature maps are compared and $\mathcal{L}_F$ is determined based on the value summing up the all comparison values. The loss is computed across all patient slice features and respective bag-level features, herein considered as augmentations per mini-batch. The total loss function of the entire framework is defined as:

$$\mathcal{L} = \lambda \mathcal{L}_B + (1-\lambda)\mathcal{L}_F, \quad \text{Equation 6}$$

where λ is a parameter to weight the contribution of the bag and constrastive losses, respectively, and the value of λ is between 0 and 1.

The detailed algorithm is presented in Algorithm.

[Algorithm Table]
Algorithm 1 DA-CMIL Algorithm

1: input: parameters $\theta_F, \theta_{\mathcal{A},S}, \theta_{\mathcal{A},T}, \theta_{\mathcal{H}}$, weight λ, epoch T, temperature τ
2: Initialize parameters $\theta_F, \theta_{\mathcal{A},S}, \theta_{\mathcal{A},T}, \theta_{\mathcal{H}}$
3: for t = 1, 2, . . . , T do
4: preprocess CT scans $S_n$ and create bags with j slices
5: obtain features: $g_{ij} = \mathcal{F}_\theta(s_{ij})$
6: spatial pooling: $\phi_{ij} = \mathcal{A}_{\theta,S}(g_{ij})$
7: obtain attention weights $a_n$ with Eq. (4) using $\mathcal{A}_{\theta,1}(\varphi_{ij})$
8: combine instance features to get z with Eq. (3)
9: obtain bag predictions: $\hat{y} = \mathcal{H}_{\mathcal{B}}(z_i)$
10: collect z and z': bag and instance features
11: normalize z and z' with $l_2$ norm.
12: compute cost in Eq. (6): $\lambda \mathcal{L}_B(\hat{y}, y_i) + (1-\lambda)\mathcal{L}_F(z', z, \tau)$
13: update parameters $\theta_F, \theta_{\mathcal{A},S}, \theta_{\mathcal{A},T}, \theta_{\mathcal{H}}$
14: endfor
15: output: $\theta_F, \theta_{\mathcal{A},S}, \theta_{\mathcal{A},T}, \theta_{\mathcal{H}}$ In the present disclosure, the inventors collected a chest CT dataset comprised of 173 samples at Yeungnam University Medical Center (YUMC), in Daegu, South Korea. The dataset includes 75 CT examples for patients with COVID-19, and 98 examples from patients with bacterial pneumonia collected between February and April, 2020. The study was approved by the Institutional Review Board (IRB) of Yeungnam University Hospital. COVID-19 patients were confirmed by RT-PCR assay of nasal and pharyngeal swab samples.

In the MIL framework, 2D CT slice or patches can be used as instances, thus we evaluate our method on both cases. In addition, a 3D CT volume dataset is also processed for training/testing 3D based methods under fully supervised settings.

Figure 3:
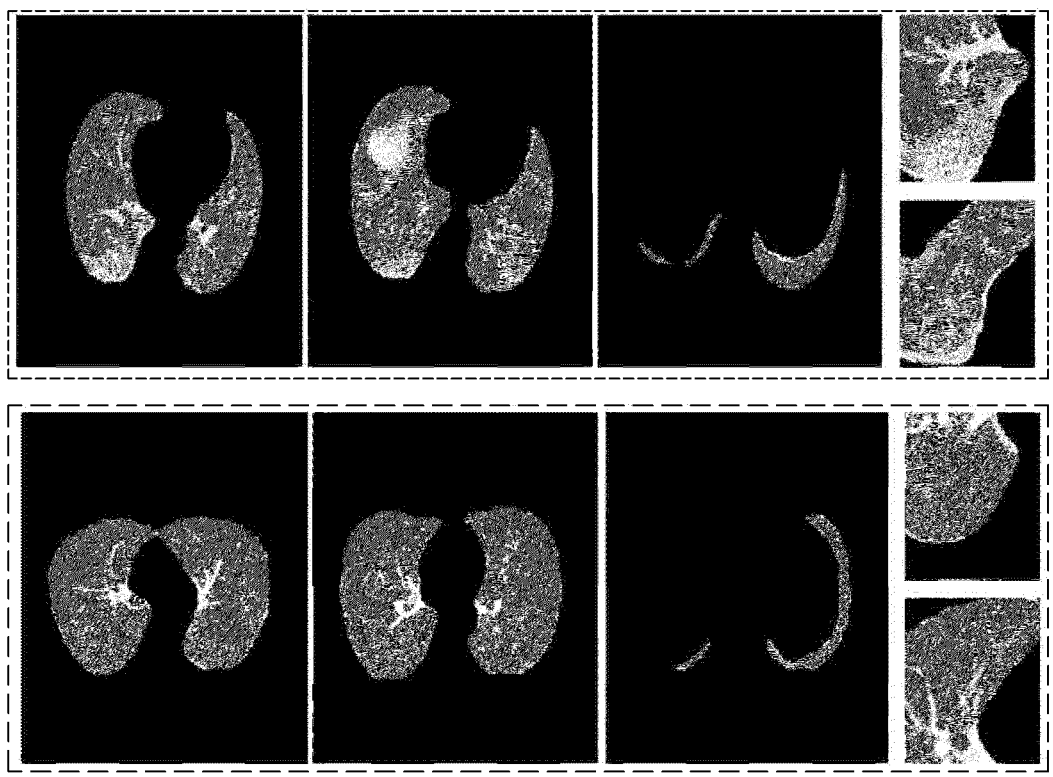
FIG. 3 is an illustration of an example of pre-processed CT images in a multiple instance learning method according to an embodiment of the present disclosure.

For pre-processing, lung regions were segmented for all CT examples. To achieve this, we employed a ResNeSt Zhang et al. (2020a) model for segmentation training and inference. The model was trained on two public datasets i.e. non-small cell lung cancer (NSCLC) Aerts et al. (2014) and COVID-19 lung infection dataset June et al. (2020). Herein, a total of 50,756 lung slices were used for training and evaluated on 1,222 independent slices. FIG. 3 shows examples of CT slices and patches employed.

FIG. 3 is an illustration of an example of pre-processed CT images in a multiple instance learning method according to an embodiment of the present disclosure.

In FIG. 3, the upper images are pre-processed images of lung CT slice(3 images on the left) of COVID-19 pneumonia patient and pre-processed images of patch samples(2 images on the right edge) of COVID-19 pneumonia patient. The lower images are pre-processed images of lung CT slice(3 images on the left) of bacterial pneumonia patient and pre-processed images of patch samples(2 images on the right edge) of bacterial pneumonia patient.

Accordingly, all the datasets were split into training, validation and testing by patient IDs with ratios 0.5, 0.1, and 0.4, respectively. The same split was used across all the dataset variants with all versions using only cropped lung regions. CT examples were 512×512, 128×128 and 256×256×256 in size for the slices, patches and 3D CT volume sets, respectively. Each CT slice was resized from 512×512 to 256×256 and patch slices were resized to 256 from 128. In particular, the slices set consisted of approximately 14,000 slices, whereas the patch version yielded 64,000 patches that mainly showed 30% of lung tissue. In the case of 3D CT volumes, all slices belonging to a patient were used to construct a volume with nearest neighbor sampling applied to obtain the desired input sizes.

The proposed model was implemented in Pytorch. A ResNet-34(He et al. (2016)) finetuned from imageNet pre-trained weights was used as the feature extraction module $\mathcal{F}_\theta(\cdot)$, with a single fully connected (FC) layer employed as the bag classifier $\mathcal{H}_{\mathcal{B}}(\cdot)$. The dimension of the features was fixed to 512; this includes the feature maps obtained from $\mathcal{F}_\theta(\cdot)$ which had 512×8×8, with C=512. Following spatial pooling, features were reshaped back to 512.

Comparison Methods

To evaluate the e!cacy of the proposed method, the result of the model according to the present disclosure compared against recent MIL based methods i.e. DeepAttentionMIL, ClassicMIL and JointMIL. Also, recent 3D based methods DeCovNet and Zhang3DCN were included for comparison. For a fair evaluation, the same backbone feature extractor is used in all methods except for the 3D methods as we used the publicly available implementations.

The present disclosure presents both quantitative and qualitative results of the proposed methods. Also, ablation studies on the effect of bag size, attention modules with/without contrastive learning and the weighting parameter λ are presented.

In Table 1, DA-CMIL with contrastive loss $\mathcal{L}_F$ achieves the best overall performance of 98.6% accuracy and an AUC of 98.4%. Notably, even when $\mathcal{L}_F$ was not applied during training, our method still reports 93%(+2.9 compared to JointMIL) and 93.4%(+2.5 compared to JointMIL) in terms of accuracy and AUC over the best weakly supervised method JointMIL.

TABLE 1

| Method | Accuracy | AUC | F1 | Specificity | Sensitivity |
|---|---|---|---|---|---|
| DeCoVNet Wang et al. (2020c) | 0.831 | 0.825 | 0.8 | 0.875 | 0.774 |
| MIL Campanella et al. (2019) | 0.803 | 0.796 | 0.767 | 0.85 | 0.742 |
| DeepAttentionMIL Ilse et al. (2018) | 0.859 | 0.875 | 0.861 | 0.75 | 1 |
| JointMIL Chikontwe et al. (2020) | 0.901 | 0.909 | 0.896 | 0.85 | 0.968 |
| Zhang3DCNN Zhang et al. (2020b) | 0.93 | 0.938 | 0.925 | 0.875 | 1 |
| DA-CMIL (w/o $\mathcal{A}_{\theta,S,I}$) | 0.76 | 0.72 | 0.62 | 1.0 | 0.45 |
| DA-CMIL (w/o $\mathcal{L}_F$) | 0.93 | 0.934 | 0.923 | 0.9 | 0.968 |
| DA-CMIL (w/ $\mathcal{L}_F$) | 0.986 | 0.984 | 0.984 | 0.975 | 1 |

To further validate the proposed method, we applied DACMIL to randomly cropped patches of the CT samples. As shown in Table 2, performance was consistently better than the compared methods.

TABLE 2

| Method | Accuracy | AUC | F1 | Specificity | Sensitivity |
|---|---|---|---|---|---|
| MIL Campanella et al. (2019) | 0.845 | 0.852 | 0.836 | 0.8 | 0.903 |
| DeepAttentionMIL Ilse et al. (2018) | 0.845 | 0.859 | 0.845 | 0.75 | 0.968 |
| JointMIL Chikontwe et al. (2020) | 0.845 | 0.837 | 0.814 | 0.9 | 0.774 |
| DA-CMIL (w/o $\mathcal{A}_{\theta,S,I}$) | 0.718 | 0.728 | 0.714 | 0.65 | 0.806 |
| DA-CMIL (w/o $\mathcal{L}_F$) | 0.873 | 0.88 | 0.866 | 0.825 | 0.935 |
| DA-CMIL (w/ $\mathcal{L}_F$) | 0.958 | 0.955 | 0.951 | 0.975 | 0.935 |

Figure 4:
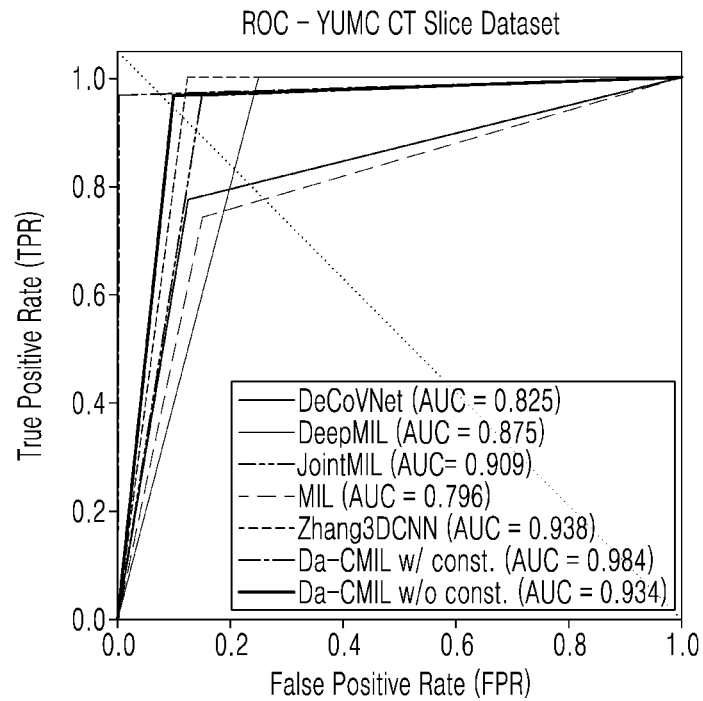
FIG. 4 illustrates graphs comparing characteristics of the multiple instance learning model according to an embodiment of the present disclosure and other learning models.
Figure 4:
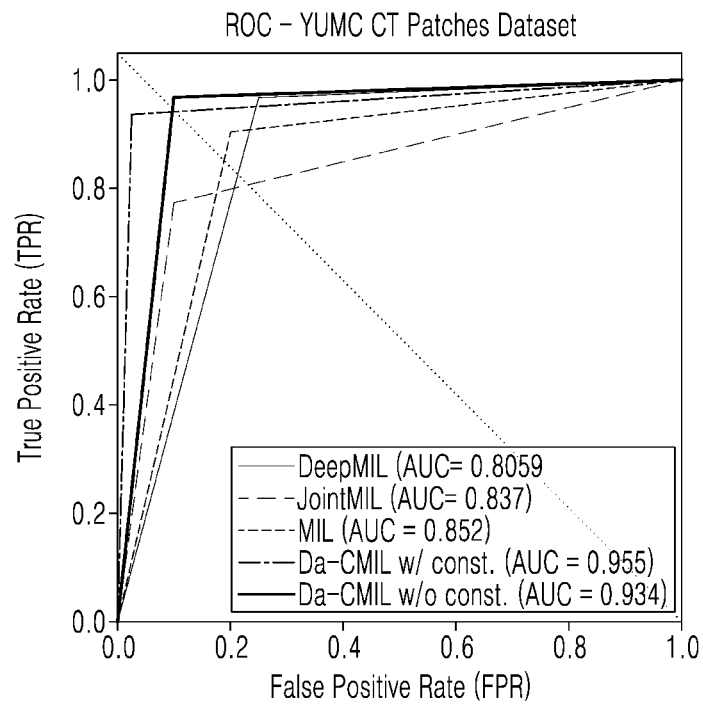

FIG. 4 illustrates graphs comparing characteristics of the multiple instance learning model according to an embodiment of the present disclosure and other learning models.

Figures 6, 7:
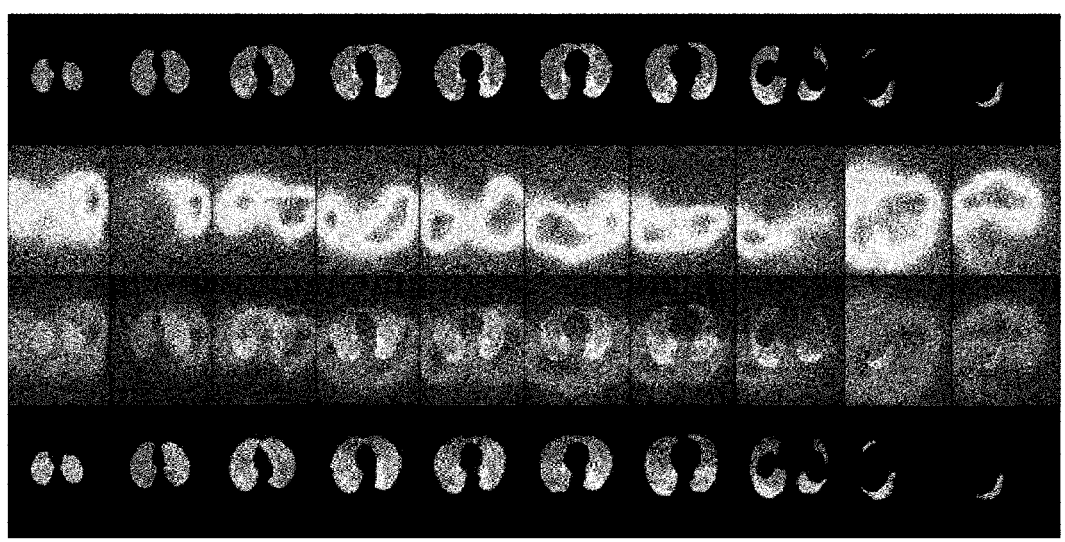
FIG. 6 illustrates graphs comparing prediction performances of the multiple instance learning model according to another embodiment of the present disclosure and other learning models on a CT patch dataset.
FIG. 7 illustrates spatial attention maps and instance attention scores derived by the multiple instance learning model according to an embodiment of the present disclosure.

FIG. 4 shows the receiver operating characteristic(ROC) curves of the compared methods on different datasets. FIG. 5 illustrates graphs comparing prediction performances of the multiple instance learning model according to an embodiment of the present disclosure and other learning models on a CT slice dataset. FIG. 6 illustrates graphs comparing prediction performances of the multiple instance learning model according to another embodiment of the present disclosure and other learning models on a CT patch dataset.

Referring to FIG. 4, overall, the proposed method shows a higher TPR and lower FPR across all settings. This is further evidenced in the summaries of the confusion matrices of the comparison methods as presented in FIGS. 5 and 6. This indicates DA-CMIL can be viable option for accurate and robust screening of COVID-19. Here, CP means Common Pneumonia or Bacterial Pneumonia and NCP means COVID-19 Pneumonia.

Effects of the Bag Size, the Weight Parameter $\lambda$ and Dual-Attention Modules on Learning To assess the effect of bag size during training on the proposed method, we performed an ablation study where the bag was constructed by varying k i.e. each bag consisted of k max instances (slices/patches). As shown in Table 3, as the bag size increases DA-CMIL performance improves.

TABLE 3

| Method | Accuracy | AUC | F1 | Specificity | Sensitivity |
|---|---|---|---|---|---|
| DA-CMIL (w/ k = 8) | 0.93 | 0.934 | 0.923 | 0.9 | 0.968 |
| DA-CMIL (w/ k = 16) | 0.944 | 0.939 | 0.933 | 0.975 | 0.903 |
| DA-CMIL (w/ k = 24) | 0.944 | 0.943 | 0.935 | 0.95 | 0.935 |
| DA-CMIL (w/ k = 32) | 0.986 | 0.988 | 0.984 | 0.975 | 1 |

DA-CMIL uses contrastive feature learning of multiple instances with a weighting parameter $\lambda$ to balance the effect of the losses. When $\lambda=1.0$, $\mathcal{L}_F(\cdot)$ has no effect on learning and showed a lower performance of 93% compared to using $\mathcal{L}_F(\cdot)$ i.e. when $\lambda<1.0$.

TABLE 4

|  | $\lambda = 0.1$ | $\lambda = 0.5$ | $\lambda = 0.9$ | $\lambda = 1.0$ |
|---|---|---|---|---|
| Accuracy | 0.972 | 0.986 | 0.986 | 0.932 |

In order to assess the effect of attention in the proposed framework, the present disclosure considers several settings where both contrastive and attention modules are either employed or not (Tables 1 and 2).

Formally, when attention is excluded, the framework would require modification in two aspects; (1) without spatial attention-based pooling of features ($\mathcal{A}_{\theta,S}$), we default to using global average pooling (GAP) of instance features for simplicity, and (2) without attention based bag-level feature aggregation via ($\mathcal{A}_{\theta,I}$), one may opt for using the mean of instance features to obtain the overall bag-level feature z alongside z'. Following these modifications, evaluation can be easily performed.

Evidently, the best performance was achieved when both $\mathcal{L}_F$ and $\mathcal{A}_{\theta,S,I}$ were part of learning. On the other hand, when the attention modules were excluded, significant reductions in the overall performance were noted i.e. −20% compared to the best performing method (Table 1). Similar performance drops were noted on the CT patch dataset (Table 2).

Using the contrastive feature loss alone without any attention modules highlighted worsened results without any performance gains over the compared methods. This serves to show the benefit of the combination of the proposed techniques (i.e. both attention and the feature loss), reporting improved results via complementary learning.

Qualitative Results

FIG. 7 illustrates spatial attention maps and instance attention scores derived by the multiple instance learning model according to an embodiment of the present disclosure.

In FIG. 7, qualitative results are presented based on spatial attention maps and attention scores, respectively. This demonstrates that DA-CMIL is able to find key slices related to infected areas with coarse maps (FIG. 7). Interestingly, low attention scores were observed for slices such as noisy slices/artifacts with no infected areas further indicating the utility of our method. Moreover, attention maps focus on key areas such as ground-glass opacities and consolidations, both consistent with clinical findings.

The present disclosure may also highlight attention maps when contrastive learning is not applied during. In general, results show similar maps as with the case when the loss is applied. However, localization of key regions is slightly degraded, especially with huge differences in the attention scores, whereas for some CT slices, both spatial maps and scores had marginal changes.

This is largely expected since the contrastive loss is aimed at encouraging similarity between representative features of a subject. The benefit of using both losses is better verified via quantitative assessment of classification performance. It is inferred that the proposed mechanism of attention is still relevant in both cases and can be highly beneficial in clinical evaluation.

In addition, according to clinical literature on similar studies, Bilateral multi-focal ground-glass opacities (GGO) in the lower lobes are the most common initial findings on CT, with other characteristics such as pleural thickening less commonly observed in imaging manifestations depending on the severity stage. This is consistent with the most of the spatial attention maps being largely focused in the lower regions. In general, Class Activation Maps (CAM) may not indicate exact lesion locations due to the resolution issue. Moreover, it should be noted that enforcing the model to produce tissue-constrained maps is challenging especially in the weakly supervised setting; without access to the actual lesion locations, it is non-trivial for the model. Herein, it is confident in the current results even when the maps are normalized to the tissue region only, it is evident that the high-density regions are clinically relevant regions corresponding to lesions and/or GGOs.

Though RT-PCR is the gold standard for COVID-19 diagnosis, it is still hindered by lengthy test times, as it can take days to obtain the results. Accordingly, CT has been considered as a reasonable alternative for current testing methods as it can produce results within minutes.

The present disclosure shows a novel approach to the application deep CNNs for COVID-19 diagnosis under weak supervision with clinical implications. It is important to have a fully automated and interpretable method in actual settings for rapid evaluation. Moreover, given the subtleties that exist between COVID-19 and other pneumonia in terms of imaging characteristics that field experts find hard to differentiate, accurate diagnosis is highly relevant.

The method according to the present disclosure can be evaluated on recently curated dataset wherein only patient diagnostic labels are available without lesion infected regions of interest as is common in existing methods.

To further validate our approach, the present disclosure qualitatively showed the regions that are focused on by the model according to the present disclosure via coarse attention maps alongside attention scores. The method according to the present disclosure achieved an AUC of 98.4%, accuracy of 98.6% and a true positive rate (TPR) of 96.8%. In addition, attention maps obtained highlight key infection areas in the majority of samples with attention scores corresponding to key slices.

The present disclosure also empirically showed the benefit of using an unsupervised contrastive loss to complement the supervised learning of patient labels and may serve as a base for more complex methods. Moreover, the proposed method surpassed 3D based methods by large margins. It is inferred that this may be due to the limited size of the dataset employed as most recent methods applied to 3D CT volumes report using large cohorts in literature. In addition, since DeCoVNet was trained from scratch and has a custom deep architecture, performance was subpar.

Though ZhangCNN's performance was considerably better than the later, it still did not achieve comparable performance even when the model was trained for more epochs. It is also worth noting that models trained with extensive augmentation did not achieve any considerable improvements across the evaluation metrics, since COVID-19 and bacterial pneumonia present similar characteristics.

Figure 8:
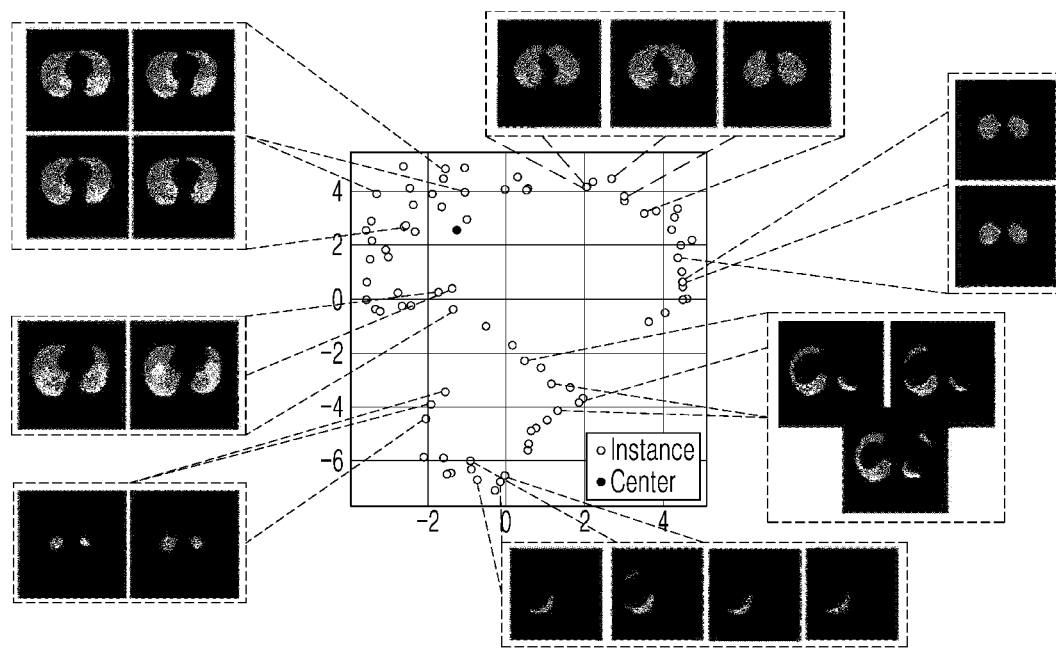
FIG. 8 illustrates CT slices represented in an embedding space in the multiple instance learning model according to an embodiment of the present disclosure.

FIG. 8 illustrates CT slices represented in an embedding space in the multiple instance learning model according to an embodiment of the present disclosure.

To further show the benefit of the proposed technique in the capturing overall statistics of a single subject, FIG. 8 presents the instance and representative features plotted in 2D space. Notably, the aggregated feature (top-left of the figure: black dot) captures of features of key slices (white or blank dot) that are well clustered together and ignores noisy artifacts in other slices. This shows that though no explicit labels are employed for instance discovery, our model is able to effectively learn which slices are useful for patient classification.

In the present disclosure, a 2D CNN framework with dual attention modules and contrastive feature learning under the multiple instance learning (MIL) framework is developed to distinguish COVID-19 and a bacterial sub-type of pneumonia in chest CTs. The present disclosure verified performance on both CT patch and slice based versions of the datasets and report results comparable to state-of-the-art methods. In addition, ablation experiments show the benefit of using large bag sizes during training and the effect of weighting losses correctly for stable learning. The present disclosure provides multiple instance learning method based on weakly supervised methods for COVID-19 screening, which enable more accurate distinguishment between COVID-19 and bacterial pneumonia.

Figure 9:
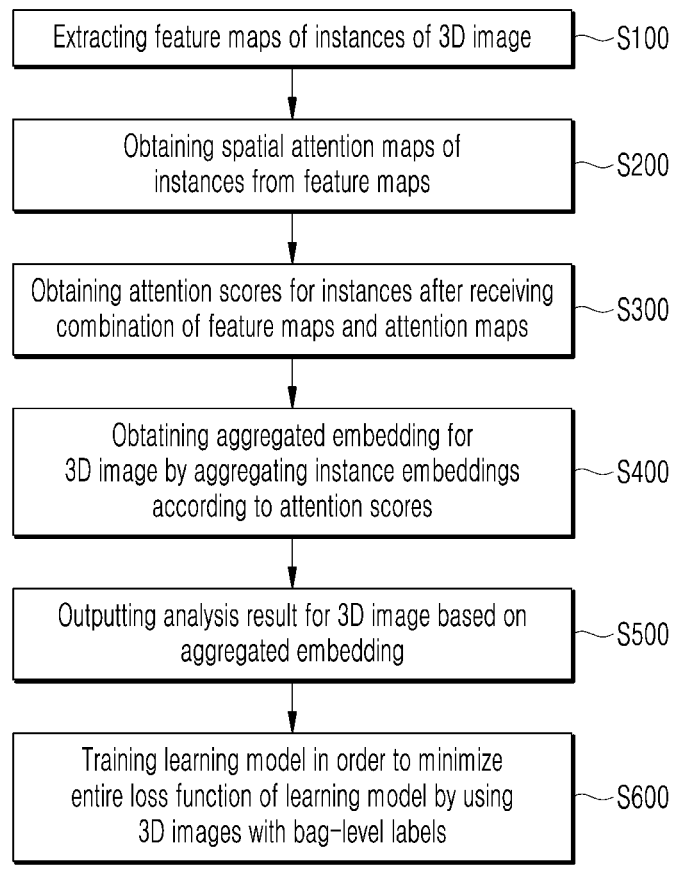
FIG. 9 is a flowchart illustrating a learning method of the multiple instance learning model according to an embodiment of the present disclosure.

FIG. 9 is a flowchart illustrating a learning method of the multiple instance learning model according to an embodiment of the present disclosure.

The multiple instance learning method for analyzing a 3D image according to an embodiment of the present disclosure may be performed by at least one processor in a computing device or a computing network.

Referring to FIG. 1, the multiple instance learning method according to an embodiment of the present disclosure may be performed by a processor 110 of a multiple instance learning device 100.

The multiple instance learning device 100 may include the processor 110 and a memory 130, and the memory 130 may store a multiple instance learning model and various instructions. Although only one memory is disclosed in FIG. 1, a memory in which the multiple instance learning model is stored and a memory in which the various instructions are stored may be configured separately.

According to the multiple instance learning method according to an embodiment of the present disclosure, the processor 110 may derive a feature map for each of 2D instances of a 3D image inputted to the multiple instance learning model (S100). A block or module for deriving such feature maps may include convolutional layers, and may be referred to as a convolution module or block.

The processor 110 may derive spatial attention maps of the instances from the feature maps derived from the convolution block (S200). A block or module for deriving such spatial attention maps may be referred to as a spatial attention block. In order for the model to analyze what is to be determined in each of the instances, the spatial attention maps may determine where parts to be emphasized are. The parameters of the initial spatial attention block may be randomly determined, but may be optimized through the training process as described above.

Thereafter, the processor 110 may derive attention scores for each of the instances by receiving a result of convolving the feature maps and the spatial attention maps (S300). Here, the convolution of the feature maps and the spatial attention maps may be element-wise multiplication. In addition, the processor 110 may aggregate embeddings of instances according to the attention scores so as to derive an aggregated embedding for the 3D image. Such operations may be performed by an instance attention block (or a latent attention block). The parameters of the initial instance attention block may be randomly determined, but may be optimized through the training process as described above.

The processor 110 may output an analysis result for the 3D image based on the aggregated embedding. Here, the analysis result may indicate whether the CT scan image indicates pneumonia due to COVID-19 or pneumonia due to another disease, as described above, but may naturally also have a meaning indicated by other diseases or images. This output may be performed by an output block.

Meanwhile, 3D images of 2D instances inputted in the training process of the multiple instance learning model may be data labeled as ground-truths. Here, labeling is performed only at the bag level for 3D images, and labeling is not performed for each 2D slice. As described above, even if the 3D image is an image labeled as COVID-19 pneumonia, some of the 2D instances may not indicate lesions of COVID-19 pneumonia at all.

For the training of the multiple instance learning model, the processor 110 may perform training such that the total loss function value of the multiple instance learning model is minimized, using training data including labeled 3D images.

Here, performing training means adjusting the parameters set for the blocks used in the steps of deriving the feature maps, deriving the attention scores, and deriving the aggregated embedding, such that the total loss function (L) of the multiple instance learning model has a minimum value or is minimized.

Meanwhile, the total loss function may be a combination of a bag-level loss function (LB) for the result of the output block and a contrastive loss function (LF) between the instance embeddings and the aggregated embedding.

As described above, the present disclosure has proposed a technique capable of automatically extracting important instances together with extracting which parts of the instances play a key role in classification, by using a spatial attention structure and an instance attention structure at the same time.

In addition, a deep learning network is trained such that a distinction between a representative embedding of an instance and each instance can be well performed, by performing training directed to minimizing the contrastive loss function together with the bag-level loss function. When the proposed technique is used, features are embedded such that instances for improving bag-level classification performance are well selected, variation of the selected instances within the class is reduced, and the distance to instances of other classes is increased.

Accordingly, based on the features extracted in this way, better results can be obtained when final bag-level classification is performed. In addition, by using a spatial attention structure and an instance-level attention structure in one network, it was qualitatively confirmed that abnormal lesion sites can be relatively accurately found even with only image unit labels.

Other Embodiments of Multiple Instance Learning Method for Histopathology Classification In addition, other embodiments of the present disclosure relates to a method for digitizing images obtained using a whole-slide image (WSI) scanner, and learning the results thereof to perform histopathology classification.

The method of the present disclosure may be performed using a processor such as a microprocessor that performs the framework proposed herein, and a computing device including a storage means for storing the digitized WSIs, a memory means for temporarily recalling data when performing classification and learning, an input means capable of receiving input of a user's control command, and a display means for displaying the classification results.

In addition to the above, a WSI scanner may further be included.

The computing device may be a single device such as a personal computer, a server, a smart pad, or a smart phone, but may also be a network device including terminals that collect WSI data and a server that learns and classifies the collected WSI data.

That is, the present disclosure relates to a method that uses a computing system consisting of a single device or a network of devices, and in particular can be understood as a process executed by a processor.

Accordingly, the subject that performs each step of the present disclosure may be referred to by different expressions, but may be an ordinary processor, even if not specifically mentioned.

Figure 10:
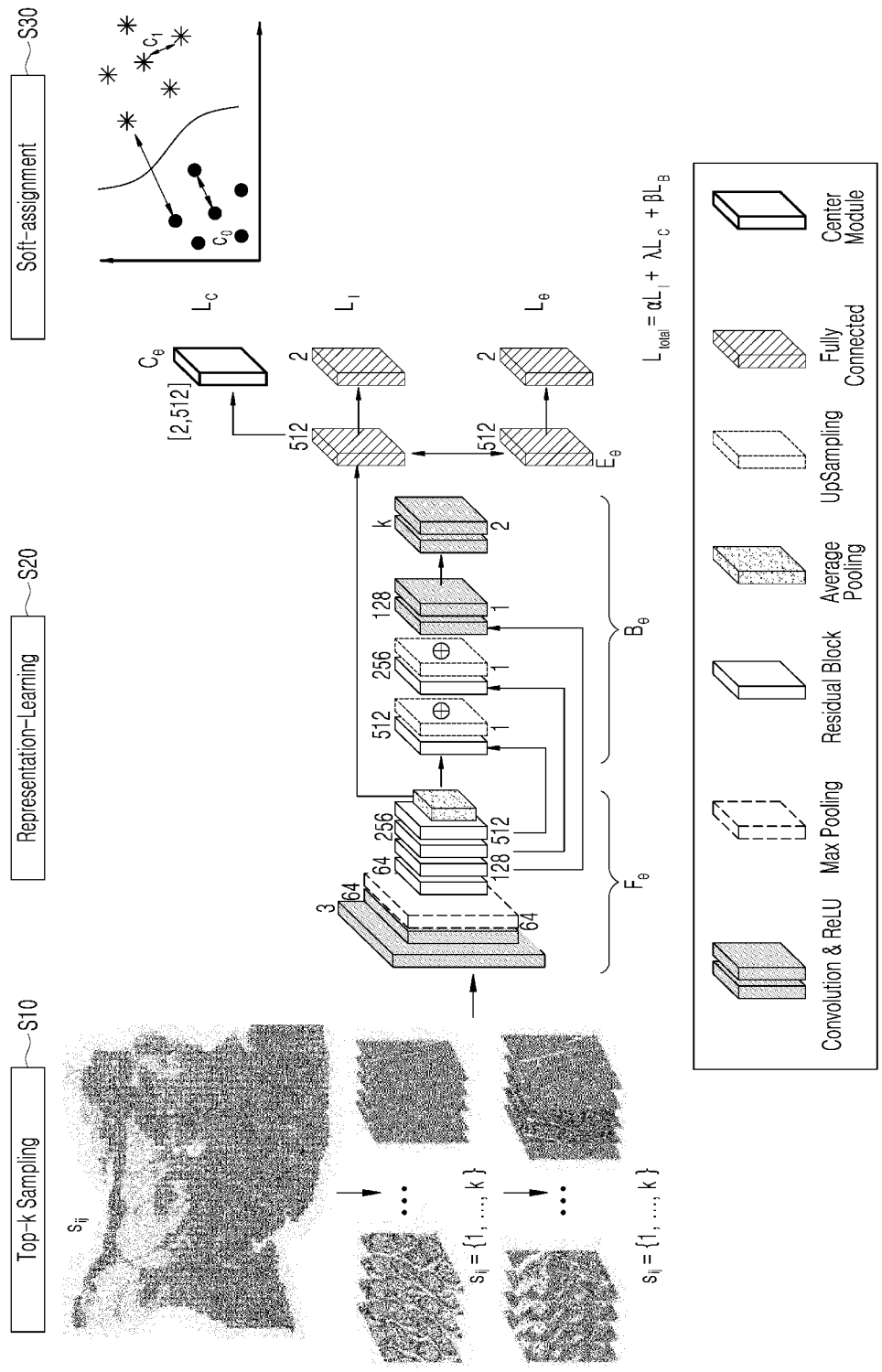
FIG. 10 is a framework of a method for multiple instance learning for histopathology classification according to another embodiment of the present disclosure.

FIG. 10 shows a framework of a method for multiple instance learning for histopathology classification according to a preferred embodiment of the present disclosure.

Referring to FIG. 10, the present disclosure includes an instance selection step of sampling k instances based on top predicted probabilities per slide (S10), a learning step of learning using the instances obtained in the instance selection step S10 (S20), and a soft-assignment-based inference with learned centers (S30).

Hereinafter, the configuration and action of the present disclosure, made up of the steps and elements as described above, will be described in more detail.

Before beginning the detailed description of the present disclosure, some definitions will be made.

A WSI dataset D may be expressed as $\{S_1, \ldots, S_n\}$.

Here, each $S_i$ (where i is 1 to n, n being a positive integer) is a WSI with a label $y_i$, and each label has a value of 0 or 1.

$S_i$, which constitutes data included in the WSI dataset, may have m instances.

That is, $S_i$ may be expressed as $\{s_{i1}, s_{i2}, \ldots, s_{im}\}$.

Here, m is a positive integer obtained from non-background regions of a slide and is equal to or less than M, where M is the total number of instances in the slide.

In the present disclosure, in order to assign the correct label $y_i$ to each slide, only set labels may be used during training, with 1 indicating positive and 0 indicating negative.

Multiple instance learning (MIL) must satisfy the following conditions:

If data $S_i$ is negative, then all instances in $S_i$ should be negative. That is, if the instance label $y_i$ is 0, then $\forall(y_{ij})$ should be 0.

If data $S_i$ is positive, then at least one instance of $S_i$ should be positive. That is, if the instance label $y_i$ is 1, $\Sigma y_{ij}$ should be equal to or greater than 1.

In order to satisfy these conditions, the present disclosure proposes a learning model (a convolutional neural network [CNN] model) capable of performing both instance level discrimination and slide level classification in an end-to-end framework as shown in FIG. 10.

First, in the instance selection step (S10), a feature extraction model $F_\theta(\cdot)$, which is a neural network, is implemented to transform an instance from an i-th slide into a low dimensional embedding $g_{ij}$.

The low dimensional embedding $g_{ij}$ may be expressed as $F_\theta(s_{ij})$.

This transformation is realized via an instance branch ($L_I$) with a shared embedding module $E_\theta$.

Thereafter, a classification module outputs the positiveness of an instance $p_{ij}$.

Here, the positiveness output uses a binary classifier $H_I$, and as mentioned above, 1 indicates positive and 0 indicates negative.

The binary classifier $H_I$ that classifies the instance $p_{ij}$ may be expressed as $H_I(p_{ij})$.

Thereafter, instance level probabilities from all bags are sorted to obtain top-most instances per slide for training.

That is, in the present disclosure, not all of the data D is used, but a selected k pieces of data $D_k$ are used. This is referred to as top-k instance selection.

Here, the selected data $D_k$ is a subset of the data D.

In this process, parameters F, E, and θ of a bag module B to be described below, like other modules, are not updated or stored.

In other words, in the instance selection step of the present disclosure, k instances are sampled at the start of each training based on the highest predicted probabilities per slide, via an instance module.

Then, using the obtained k instances, the learning step (S20) is performed.

The learning step (S20) of the present disclosure includes instance-level learning and bag-level learning.

That is, learning is performed considering both the instance level and the bag level.

First, in the instance-level learning, for a given k instance input in each training step, embeddings $g_{ij}$ are obtained after global average pooling via a neural network $F_\theta$.

The obtained embeddings $g_{ij}$ are supplied to a shared embedding module $E_\theta$, and a predicted value for an instance classifier ($H_I$) can be obtained using cross-entropy.

Here, the k instance input $s_{ij}$ is included in the set of the k pieces of data $D_k$.

Each instance is assigned a bag-level label y, and satisfies the above conditions and is used to compute an instance loss $L_I$.

The equation for calculating instance loss may be expressed by Equation 7 as follows.

$$\mathcal{L}_I = -\Sigma\, y_{ij} \log p_{ij} \qquad \text{Equation 7}$$

Further, in pyramidal bag-level learning $B_\theta$, three feature maps obtained from the instance-level learning are used, in addition to the previously obtained embeddings $g_{ij}$.

The three feature maps are low dimensional embeddings, instances, and instance level probabilities of bags.

The three feature maps are inputted to a series of convolutional blocks with input sizes [512, 256, 128] corresponding to the feature map size, and features each reduced to a single channel can be obtained.

Then, the maps are upsampled to match the size of the previous block using linear interpolation for matching the size of the previous block and concatenating with the previous feature map, and a single spatial map with k channels, used to obtain a final flattened feature $z_i$ by concatenating with the previous feature map, is obtained.

Thereafter, the final flattened feature $z_i$ is inputted to a bag classifier $H_B(z_i)$ via the shared embedding module $E_\theta$.

Bag predictions ($\acute{y}$) are used to obtain a bag loss $L_B(\acute{y}, y_i)$ using cross-entropy.

The equation for obtaining the bag loss is shown as Equation 8 below.

$$\mathcal{L}_B = -\sum y_i \log \hat{y}. \qquad \text{Equation 8}$$

In addition, in order to improve the discriminating ability of deep features, the present disclosure introduces the concept of center loss.

Center loss characterizes intra-class variations by learning embeddings that minimize the distance of instances from the same bag.

The center loss may be expressed by Equation 9 as follows.

$$\mathcal{L}_C = \frac{1}{2}\sum_{i=1}^{u} \|g_{ij} - c_{y_i}\|_2^2. \qquad \text{Equation 9}$$

In Equation 9, $c_{yi}$ is the $y_{ij}$-th class center's deep features with the same dimension as the embedding $g_{ij}$, and u is the mini-batch size.

In the present disclosure, class centers are parameterized by a center module $C_\theta(\bullet)$ that is initialized from a standard normal distribution and trained jointly with a center loss $L_C$ and a bag loss $L_B$.

Intuitively, instance embeddings from the same bag should have similar features that can cluster to similar points in the embedding space.

The class centers are updated based on instance embeddings of a mini-batch rather than the entire dataset.

The final loss function may be expressed by Equation 10 as follows.

$$\mathcal{L}^* = \alpha \mathcal{L}_I + \lambda \mathcal{L}_C + \beta \mathcal{L}_B \qquad \text{Equation 10}$$

In the above Equation 10, $\alpha$, $\beta$ and $\lambda$ are each loss balance parameters.

Next, in the soft-assignment-based inference step (S30), for accurate classification when considering a bag embedding obtained via the bag-level learning, it is necessary to assign the correct label as a final diagnosis.

To this end, instance embeddings of the same bag should be matched with a single centroid that represents the bag label.

A bag-level embedding $z_i$ for a slide $S_i$ is $B\{g_{i1}, \ldots, g_{ik}\}$, and the bag-level embedding $z_i$ may be assigned to the learned centroid via Equation 11, which is a kernel that detects the similarity between two points.

$$q_i = \frac{(1 + \|z_i - c_{y_i}\|^2/\varphi)^{-\frac{\varphi+1}{2}}}{\sum_{i'} (1 + \|z_i - c_{y_{i'}}\|^2/\varphi)^{-\frac{\varphi+1}{2}}} \qquad \text{Equation 11}$$

In Equation 11, $q_i$ is the probability of assigning the bag-level embedding $z_i$ to a class center, and $\psi$ are the degrees of freedom of a Student's distribution.

In the above example, the label of a slide unit is determined based on the predicted value obtained from the center loss part and the distance of the center loss. As another example, a predicted value obtained from the bag level loss may be determined.

In addition, in the present disclosure, when learning is performed, labels of instance level units are not provided, but a predicted value may be obtained in instance units.

If instances can be predicted, malignant regions (tumors) can be automatically detected.

The above-mentioned multiple instance learning for histopathology classification can be performed by at least one processor in a computing device or a computing network. The method for the above-mentioned multiple instance learning for histopathology classification may include an instance selection step of implementing a feature extraction model $F\theta(\bullet)$ to transform instances $p_{ij}$ from an i-th slide into a low dimensional embedding gij, and after checking a positiveness of the instance pij using an initial binary classifier(having random parameter), sampling top-most instances per slide for training for sampling the k instances that have the highest probabilities based on instance level probabilities of all bags including the slides.

Afterwards, a learning step of learning using the instances obtained in the instance selection step, wherein instance-level learning and bag-level learning are performed in order to minimize instance level loss and bag level loss by optimizing parameters of the entire model(including instance level loss function, bag level loss function, center loss function, $F_\theta$ and $G_\theta$), can be performed.

Here, center loss function is configured to make instances in the same class closer, and instances in the different class more distant.

The learning step can be characterized by obtaining an instance loss, a bag loss, and a center loss.

An example of an experiment in which histopathology classification is performed using the method of the present disclosure configured as described above, and the results thereof, will be described below.

Dataset and Settings

As an embodiment of the present disclosure, two colectoral cancer (CRC) datasets collected at an anonymous medical center and scanned under different scanning conditions were prepared.

The datasets include Hematoxylin and Eosin stained normal and malignant tissue slides that were scanned at ×40 magnification using different scanners.

CRC is the third most common cancer in humans, and a common cause of death in both males and females.

In the datasets, malignant slides contain microsatellite instable (MSI) CRC, which is a molecular phenotype due to defective DNA.

Expert pathologists detect and treat MSI using immunohistochemical analysis (IHC) and PCR-based amplification. Determination of MSI status in CRC has prognostic and therapeutic implications.

Of the two datasets, a first dataset consists of 59 normal and 114 malicious WSIs, to a total of 173 WSIs, and a second dataset consists of 85 normal and 108 malicious WSIs, to a total of 193 WSIs.

In the present disclosure, the datasets were divided into non-overlapping sets of 40%, 10%, and 50% of the total, for training, verification, and testing, respectively.

Then, for each WSI, after conversion to HSV color space, the method described in Otsu, N.: A threshold selection method from gray-level histograms. IEEE transactions on systems, man, and cybernetics 9(1), 62-66 (1979), was applied to remove non-tissue regions.

Patch candidate locations were selected randomly for extraction per slide during training and validation, respectively.

During training and inference, the number of instances k was set to 50, and instances having a size of 256×256 were used.

A ResNet-34, from He, K., Zhang, X., Ren, S., and Sun, J.: Deep residual learning for image recognition. In: Proceedings of the IEEE conference on computer vision and pattern recognition. pp. 770-778 (2016), was fine-tuned and used as the feature extraction model $F_\theta$.

In addition, Fully Connected layers were used for the instance and bag classifiers $H_I$ and $H_B$.

The number of features of the embeddings and center module was set to 512, and the entire framework was trained end-to-end at a learning rate of $1e^{-4}$ for 40 epochs.

Further, the loss balance parameters $\alpha$, $\beta$, and $\lambda$ were set to 1.0, 0.01, and 0.01, respectively. That is, loss balance parameters may be set to arbitrary positive decimal values.

Comparison Methods

In order to explain the effects of the present disclosure, the classification results will be compared with those of the technique in Campanella, G., Hanna, MG, Geneslaw, L., Miraor, A., Silva, V W K, Busam, K J, Brogi, E., Reuter, V E, Klimstra, D S, and Fuchs, T J: Clinical-grade computational pathology using weakly supervised deep learning on whole slide images. Nature medicine 25(8), 1301-1309 (2019), which represents the state-of-the-art technique in the technical field to which the present disclosure belongs. The above method will hereinafter be abbreviated to "comparison technique 1".

In addition, the present disclosure is evaluated against the techniques in Ilse, M., Tomczak, J M, and Welling, M.: Attention-based deep multiple instance learning. arXiv preprint arXiv: 1802.04712 (2018) (hereinafter, "comparison technique 2"), and in Nazeri, K., Aminpour, A., and Ebrahimi, M.: Two-stage convolutional neural network for breast cancer histology image classification. In: International Conference Image Analysis and Recognition. pp. 717-726. Springer (2018) (hereinafter, "comparison technique 3").

For a fair comparison, the same backbone $F_\theta$ is used in all cases.

Both comparison technique 1 and comparison technique 3 use a two-stage learning procedure of instance-level learning and slide-level aggregation.

Comparison technique 2 uses an end-to-end approach with permutation invariant pooling based on an attention mechanism.

Quantitative Results

Table 5 below is a performance comparison table showing a comparison of the classification results of the first dataset of the present disclosure and the comparison techniques.

TABLE 5

| Method | F1Score | Precision | Recall | Accuracy |
|---|---|---|---|---|
| Comparison Technique 1 | 76.8 | 84.46 | 79.49 | 79.49 |
| Comparison Technique 1 + RNN | 80.16 | 85.98 | 82.05 | 82.05 |
| Comparison Technique 2 | 85.95 | 86.03 | 85.90 | 85.90 |
| Comparison Technique 3 | 65.21 | 80.41 | 71.79 | 71.79 |
| Ours (w/o center loss) | 86.93 | 87.2 | 87.18 | 87.18 |
| Ours (w/ all loss + bag) | 86.77 | 87.58 | 87.18 | 87.18 |
| Ours (w/ all loss + soft) | 92.36 | 92.54 | 92.31 | 92.31 |

As shown in Table 5, the method of the present disclosure including the soft-assignment based inference step (S30) achieved the best results.

Comparison technique 1 considers the probability of the top-most instance as the final slide, and thus performance is reduced.

In addition, when the present disclosure was evaluated using bag classification only, 9.97% improved performance was achieved compared to comparison technique 1, and the assignment-based approach showed an improvement of 15.56%.

Particularly, comparison technique 2 was the best among the compared methods showing the advantages of attention-based aggregation. However, application of the bag module of the present disclosure can further improve performance over that described in comparison technique 2.

In most cases, soft-assignment is an excellent alternative to bag classifiers, and in the present disclosure, it is argued that since the learned centers have the maximum information among other similar instance embeddings, the soft-assignment-based inference step (S30) shows more robust performance than other methods that use a bag classifier.

Table 6 below is a performance comparison table showing a comparison of the classification results of the second dataset of the present disclosure and the comparison techniques.

TABLE 6

| Method | F1Score | Precision | Recall | Accuracy |
|---|---|---|---|---|
| Comparison Technique 1 | 92.06 | 93.13 | 92.31 | 92.31 |
| Comparison Technique 1 + RNN | 97.41 | 97.53 | 97.44 | 97.44 |
| Comparison Technique 2 | 93.65 | 94 | 93.59 | 93.59 |
| Comparison Technique 3 | 89.55 | 89.89 | 89.74 | 89.74 |
| Ours (w/o center loss) | 93.43 | 94.17 | 93.59 | 93.59 |
| Ours (w/ all loss + bag) | 97.41 | 97.53 | 97.44 | 97.44 |
| Ours (w/ all loss + soft) | 98.71 | 98.74 | 98.72 | 98.72 |

As shown in Table 6, the method of the present disclosure exhibits significantly better performance compared to the comparison techniques.

Although the RNN-based aggregation of comparison technique 1 is the best in this set, the method of the present disclosure shows a 1.28% improvement in comparison.

In addition, most of the methods showed higher performance in the second dataset compared to the first dataset. This is because performance may vary due to differences in scanning protocols.

Since the standard protocol introduced in comparison technique 1, which uses recent normalization techniques, were followed, color normalization methods were not used in pre-processing.

Qualitative Results

FIG. 11 shows qualitative results of the present disclosure in terms of two aspects: k patches, which are model samples per slide-class; and effectiveness of a learned model in interpretability via segmentation.

In clinical research, it is advantageous to view the regions that the model focuses on when making decisions to assist experts.

Accordingly, in the present disclosure, the effectiveness of the method of present disclosure is visually validated by collecting patches with a k value of 5 with both high and low positives predicted by the instance classifier.

Particularly, the instances predicted with the lowest value all correspond to actual normal tissues, while those with a high probability are malignant tumor regions that are clustered together.

This shows that the model can accurately classify ambiguous labels in each slide.

In addition, by performing patch-wise classification for entire slides using the trained model, a heat map that is thresholded and shows regions of high tumor probability can be obtained.

Notably, these predictions exactly match expert annotations.

This is because each step in the present disclosure accurately selects suspicious instances, and uses sampling to avoid false negatives.

These results validate the effectiveness of the method of the present disclosure, and show that the method of the present disclosure achieves a good balance between instance learning and bag feature learning.

The above-described embodiments according to the present disclosure may be implemented in the form of a computer program that may be executed by various components on a computer, and the computer program may be recorded in a computer-readable medium. Examples of the computer-readable media include, but are not limited to: magnetic media such as hard disks, floppy disks, and magnetic tape; optical media such as CD-ROM disks and DVD-ROM disks; magneto-optical media such as floptical disks; and hardware devices that are specially configured to store and execute program codes, such as ROM, RAM, and flash memory devices.

Meanwhile, the computer programs may be those specially designed and constructed for the purposes of the present disclosure or they may be of the kind well known and available to those skilled in the computer software arts. Examples of program code include both machine codes, such as produced by a compiler, and higher level code that may be executed by the computer using an interpreter.

As used in the present disclosure (particularly in the appended claims), the singular forms "a," "an," and "the" include both singular and plural references, unless the context clearly states otherwise. Also, it should be understood that any numerical range recited herein is intended to include all sub-ranges subsumed therein (unless expressly indicated otherwise) and accordingly, the disclosed numeral ranges include every individual value between the minimum and maximum values of the numeral ranges.

The order of individual steps in process claims according to the present disclosure does not imply that the steps must be performed in this order; rather, the steps may be performed in any suitable order, unless expressly indicated otherwise. The present disclosure is not necessarily limited to the order of operations given in the description. All examples described herein or the terms indicative thereof ("for example," etc.) used herein are merely to describe the present disclosure in greater detail. Therefore, it should be understood that the scope of the present disclosure is not limited to the exemplary embodiments described above or by the use of such terms unless limited by the appended claims. Also, it should be apparent to those skilled in the art that various modifications, combinations, and alternations may be made depending on design conditions and factors within the scope of the appended claims or equivalents thereof.

While specific exemplary embodiments of the present disclosure have been described above and illustrated, it will be understood by those skilled in the art that the present disclosure is not limited to the described exemplary embodiments, and various changes and modifications may be made to the present disclosure without departing from the spirit and the scope of the present disclosure. Therefore, the true technical scope of the present disclosure is not limited to the above-described exemplary embodiments, but shall be defined by the following claims.

What is claimed is:

1. A multiple instance learning device for analyzing 3D images, comprising:
    a memory in which a multiple instance learning model is stored; and
    at least one processor electrically connected to the memory,
    wherein the multiple instance learning model comprises:
    a convolution block configured to derive a feature map for each of 2D instances of a 3D image inputted to the multiple instance learning model;
    a spatial attention block configured to derive spatial attention maps of the instances from the feature maps derived from the convolution block;
    an instance attention block configured to receive a result of combining the feature maps and the spatial attention maps and derive an attention score for each instance, and derive an aggregated embedding for the 3D image by aggregating embeddings of the instances according to the attention scores; and an output block configured to output an analysis result for the 3D image based on the aggregated embedding.

2. The multiple instance learning device of claim 1, wherein the at least one processor is configured to perform an operation of, in a training phase of the multiple instance learning model, training the multiple instance learning model such that a total loss function (L) of the multiple instance learning model has a minimum value, using training data including 3D images labeled with ground-truths for the analysis result, wherein the total loss function is a combination of a bag-level loss function ($L_B$) for a result of the output block and a contrastive loss function ($L_F$) between the instance embeddings and the aggregated embedding.

3. The multiple instance learning device of claim 2, wherein the operation of training the multiple instance learning model comprises an operation of adjusting parameters of the convolution block, the spatial attention block, and the instance attention block such that the total loss function (L) of the multiple instance learning model has a minimum value.

4. The multiple instance learning device of claim 2, wherein the total loss function (L) is expressed by Equation 1 below, $$\mathcal{L} = \lambda \mathcal{L}_B + (1-\lambda)\mathcal{L}_F \quad \text{Equation 1:}$$

wherein $\lambda$ is a value between 0 and 1 and is a parameter representing a weight of the bag-level loss function.

5. The multiple instance learning device of claim 2, wherein the bag-level loss function ($L_B$) is expressed by Equation 2 below, and the contrastive loss function ($L_F$) is expressed by Equation 3 below, $$\mathcal{L}_B = -\Sigma y_i \log \hat{y} \quad \text{Equation 2:}$$

wherein $y_i$ is an instance label; and $\hat{y}$ is the probability of the 3D image being labelled as $y_i$, $$\mathcal{L}_F(z', z, \tau) = -\log \sum_{i,j=1}^{N} \frac{\exp(sim(z'_i, z_j)/\tau)}{\sum_{k=1}^{2N} \mathbb{Q}_{[k \neq i]} \exp(sim(z'_i, z_k)/\tau)} \quad \text{Equation 3}$$

wherein z' is an instance-level feature; z is a bag-level feature; $\mathbb{Q}_{[k \neq i]} \in \{0, 1\}$ has a value of 1 if k is not equal to i and a value of 0 if k=i; $\tau$ is a temperature parameter; sim(•, •) is a similarity function; and N is the number of instances of the 3D image.

6. The multiple instance learning device of claim 1, wherein the at least one processor is configured to perform an operation of, in a training phase of the multiple instance learning model, training the multiple instance learning model such that a final loss function (L*) of the multiple instance learning model has a minimum value, using training data including 3D images labeled with ground-truths for the analysis result, wherein the final loss function is a combination of a bag-level loss function ($L_B$) for a result of the output block, ins and an instance-level loss function ($L_I$), and a center loss function ($L_c$).

7. The multiple instance learning device of claim 6, wherein the final loss is expressed by Equation 4 as follows:

$$\mathcal{L}^* = \alpha \mathcal{L}_I + \lambda \mathcal{L}_C + \beta \mathcal{L}_B \quad \text{Equation 4:}$$

wherein L is the final loss, $L_I$ is the instance loss, $L_B$ is the bag loss, $L_C$ is the center loss, and $\alpha$, $\beta$, and $\lambda$ are each loss balance parameters set to arbitrary positive decimal values.

8. A multiple instance learning device for analyzing 3D images, comprising:

a memory in which at least one instruction is stored; and
at least one processor operating in conjunction with the memory and configured to execute the at least one instruction, wherein the at least one instruction is configured to, when executed by the at least one processor, cause the at least one processor to perform operations of:

deriving a feature map for each of 2D instances of a 3D image inputted to a multiple instance learning model;

deriving spatial attention maps of the instances from the feature maps;

receiving a result of combining the feature maps and the spatial attention maps, and deriving an attention score for each instance;

deriving an aggregated embedding for the 3D image by aggregating embeddings of the instances according to the attention scores; and outputting an analysis result for the 3D image based on the aggregated embedding.

9. The multiple instance learning device of claim 8, wherein the at least one processor is configured to perform an operation of, in a training phase of the multiple instance learning model, training the multiple instance learning model such that a total loss function (L) of the multiple instance learning model has a minimum value, using training data including 3D images labeled as ground-truths for the analysis result, wherein the total loss function is a combination of a bag-level loss function ($L_B$) for a result of the output block and a contrastive loss function ($L_F$) between the instance embeddings and the aggregated embedding.

10. The multiple instance learning device of claim 9, wherein the operation of training the multiple instance learning model comprises an operation of adjusting parameters used in the operation of deriving the feature maps, the operation of deriving the spatial attention maps, the operation of deriving the attention scores, and the operation of deriving the aggregated embedding, such that the total loss function (L) of the multiple instance learning model has a minimum value.

11. The multiple instance learning device of claim 9, wherein the total loss function (L) is expressed by Equation 1 below, $$\mathcal{L} = \lambda \mathcal{L}_B + (1-\lambda)\mathcal{L}_F \quad \text{Equation 1:}$$

wherein $\lambda$ is a value between 0 and 1 and is a parameter representing a weight of the bag-level loss function.

12. The multiple instance learning device of claim 9, wherein the bag-level loss function ($L_B$) is expressed by Equation 2 below, and the contrastive loss function ($L_F$) is expressed by Equation 3 below, $$\mathcal{L}_B = -\Sigma y_i \log \hat{y} \quad \text{Equation 2:}$$

wherein $y_i$ is an instance label; and $\hat{y}$ is the probability of the 3D image being labelled as $y_i$, $$\mathcal{L}_F = -\log \frac{\exp(sim(z'_i, z_j)/\tau)}{\sum_{k=1}^{2N} \mathbb{Q}_{[k \neq i]} \exp(sim(z'_i, z_k)/\tau)} \quad \text{Equation 3}$$

wherein z' is an instance-level feature; z is a bag-level feature; $\mathbb{Q}_{[k \neq i]} \in \{0, 1\}$ has a value of 1 if k is not equal to i and a value of 0 if k=i; $\tau$ is a temperature parameter;

sim(•, •) is a similarity function; and N is the number of instances of the 3D image.

13. A multiple instance learning method for analyzing 3D images, the method performed by at least one processor in a computing device or a computing network, and the method comprising:

deriving a feature map for each of 2D instances of a 3D image inputted to a multiple instance learning model;

deriving spatial attention maps of the instances from the feature maps derived;

receiving a result of combining the feature maps and the spatial attention maps, and deriving an attention score for each instance;

deriving an aggregated embedding for the 3D image by aggregating embeddings of the instances according to the attention scores; and outputting an analysis result for the 3D image based on the aggregated embedding.

14. The multiple instance learning method of claim 13, wherein the 3D image is labelled as ground-truth for the analysis result, and wherein the multiple instance learning method further comprises, in a training phase of the multiple instance learning model, training the multiple instance learning model such that a total loss function (L) of the multiple instance learning model has a minimum value, using training data including the 3D image labeled as a ground-truth for the analysis result, wherein the total loss function is a combination of a bag-level loss function ($L_B$) for a result of the output block and a contrastive loss function ($L_F$) between the instance embeddings and the aggregated embedding.

15. The multiple instance learning method of claim 14, wherein the training of the multiple instance learning model comprises adjusting parameters used in the deriving of the feature maps, the deriving of the spatial attention maps, the deriving of the attention scores, and the deriving of the aggregated embedding, such that the total loss function (L) of the multiple instance learning model has a minimum value.

16. The multiple instance learning method of claim 14, wherein the total loss function (L) is expressed by Equation 1 below, $$\mathcal{L} = \lambda \mathcal{L}_B + (1-\lambda)\mathcal{L}_F \qquad \text{Equation 1:}$$

wherein $\lambda$ is a value between 0 and 1 and is a parameter representing a weight of the bag-level loss function.

17. The multiple instance learning method of claim 14, wherein the bag-level loss function ($L_B$) is expressed by Equation 2 below, and the contrastive loss function ($L_F$) is expressed by Equation 3 below, $$\mathcal{L}_B = -\Sigma y_i \log \hat{y}. \qquad \text{Equation 2:}$$

wherein $y_i$ is an instance label; and $\hat{y}$ is the probability of the 3D image being labelled as $y_i$, $$\mathcal{L}_F = -\log \frac{\exp(sim(z'_i, z_j)/\tau)}{\sum_{k=1}^{2N} \mathbb{Q}_{[k \neq i]} \exp(sim(z'_i, z_k)/\tau)} \qquad \text{Equation 3}$$

wherein z' is an instance-level feature; z is a bag-level feature; $\mathbb{Q}_{[k \neq i]} \in \{0, 1\}$ has a value of 1 if k is not equal to i and a value of 0 if k=i; $\tau$ is a temperature parameter; sim (•, •) is a similarity function; and N is the number of instances of the 3D image.

* * * * *